United States Patent [19]

Kondo et al.

[11] Patent Number: 4,904,668
[45] Date of Patent: Feb. 27, 1990

[54] BENZOYL UREA COMPOUND

[75] Inventors: Nobuo Kondo, Daito; Masahiro Kikuchi, Mino; Tsunetaka Nakajima, Kashiwara; Masahiro Watanabe, Akashi; Kazumasa Yokoyama, Toyonaka; Takahiro Haga, Kusatsu; Nobutoshi Yamada; Hideo Sugi, both of Moriyama; Toru Koyanagi, Kyoto, all of Japan

[73] Assignees: Ishihara Sangyo Kaisha Ltd.; The Green Cross Corporation, both of Osaka, Japan

[21] Appl. No.: 101,005

[22] Filed: Sep. 25, 1987

[30] Foreign Application Priority Data

Sep. 29, 1986 [JP] Japan ............................ 61-230520
Jun. 30, 1987 [JP] Japan ............................ 62-164496

[51] Int. Cl.$^4$ ................. C07D 239/34; A61K 31/505
[52] U.S. Cl. ..................................... 514/274; 544/316
[58] Field of Search ...................... 544/316; 514/274

[56] References Cited

FOREIGN PATENT DOCUMENTS 1079285 6/1980 Canada .
1120480 3/1982 Canada .
  25363 3/1981 European Pat. Off. .
 169484 1/1986 European Pat. Off. .
 192235 8/1986 European Pat. Off. .

OTHER PUBLICATIONS

Haga et al., Chemical Abstracts, vol. 104, entry 207302m (1986).
Haga et al., Chemical Abstracts, vol. 105, entry 226077d (1986).
Knodo et al., Chemical Abstracts, vol. 108, entry 44042t (1988).
Nishiyama et al., Chemical Abstracts, vol. 106, entry 156284p (1987).
Chemical Abstracts, vol. 91, No. 19, Nov. 5, 1979, Columbus, Ohio, USA, Barltrop, D. et al, "Effect of Particle Size on Lead Absorption from the Gut.", p. 153, Abstract No. 152 327d & Arch. Envior. Heath, 1979, 34(4), 280-5.

Primary Examiner—John M. Ford
Attorney, Agent, or Firm—Oblon, Spivak, McClelland, Maier & Neustadt

[57] ABSTRACT

A benzoyl urea compound having the formula:

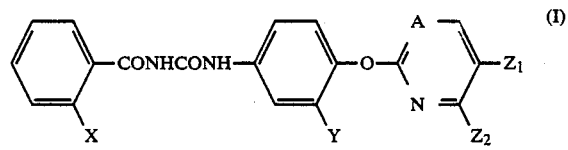

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, or the formula:

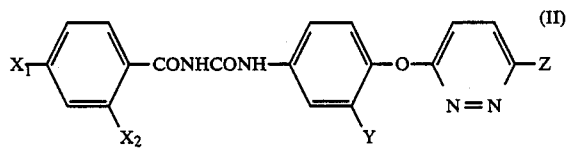

wherein each of $X_1$ is $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group, characterized in that its average particle size is not larger than 1 μm.

9 Claims, No Drawings

BENZOYL UREA COMPOUND

The present invention relates to a benzoyl urea compound represented by the following formula I or II (hereinafter referred to as a benzoyl urea compound (I) or (II)) with its average particle size being not larger than 1 μm. More particularly, the present invention relates to an antitumour benzoyl urea compound having the formula:

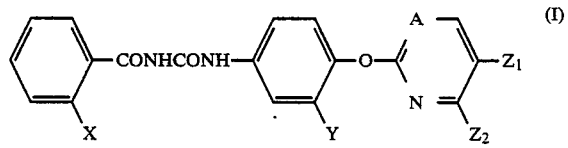

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, or the formula:

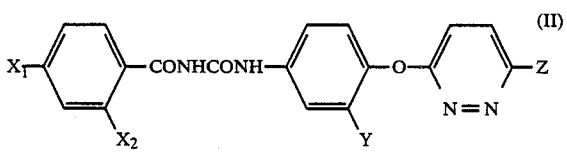

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group, having an improved absorbability through the gut.

The benzoyl urea compound (I) or (II) is substantially known to have excellent antitumour activities (Japanese Unexamined Patent Publications No. 109721/1982, No. 1670/1986, No. 33176/1986, No. 93163/1986, No. 5959/1987 and No. 116566/1987). However, this compound is hardly soluble in water, and its absorbablity through e.g. the gut is poor. Therefore, in order to obtain adequate antitumour activities, it is necessary to increase the dose, whereby there is a possible danger of adverse effects due to the excessive admistration.

It is an object of the present invention to provide a benzoyl urea compound (I) or (II) having an improved absorbability through the gut.

The present inventors have conducted extensive research with an aim to improve the absorbability of the benzoyl urea compound (I) or (II) through the gut, and as a result, have found it possible to increase the absorbability of the benzoyl urea compound (I) or (II) through the gut by adjusting the average particle size of the benzoyl urea compound (I) or (II) to a level of not larger than 1 μm. The present invention has been accomplished on the basis of this discovery.

Namely, the present invention provides a benzoyl urea compound having the formula:

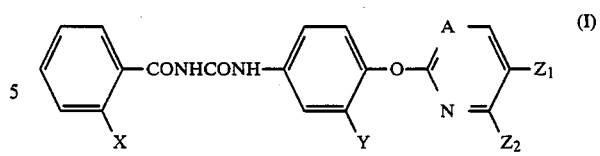

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, or the formula:

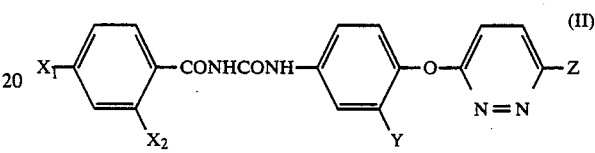

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group, characterized in that its average particle size is not larger than 1 μm.

Now, the present invention will be described in detail with reference to the preferred embodiments.

In this specification, the halogen atom is preferably a chlorine atom or a bromine atom.

The following compounds may be mentioned as typical examples of the benzoyl urea compound (I) or (II).

(Compound No. 1)
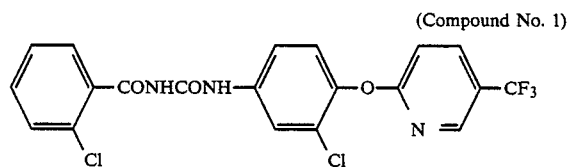

(Compound No. 2)
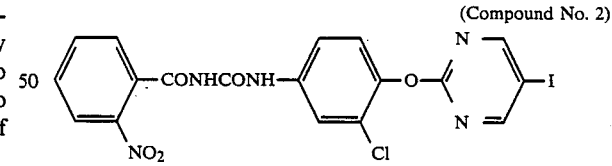

(Compound No. 3)
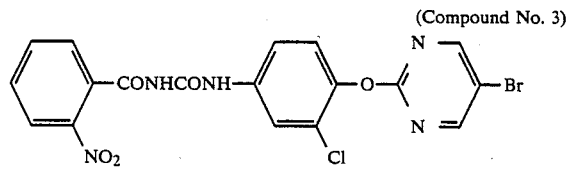

(Compound No. 4)
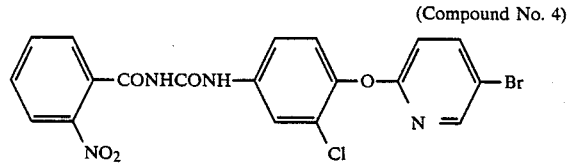

-continued

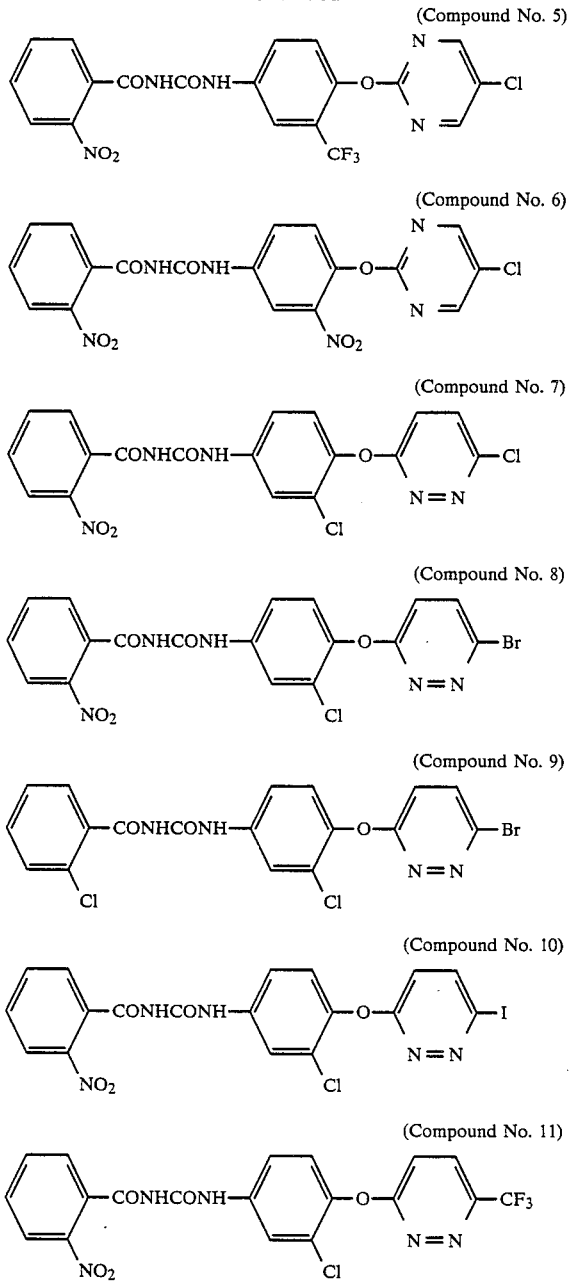

The benzoyl urea compound (I) or (II) is substantially a known compound, and it may be prepared by a method disclosed in e.g. Japanese Unexamined Patent Publication No. 109721/1982, No. 1670/1986, No. 33176/1986, No. 93163/1986, No. 227572/1986, No. 5959/1987, No. 116566/1987 or No. 135463/1987 or by a similar method.

In the present invention, the benzoyl urea compound is in the form of fine particles having an average particle size of not larger than 1 μm, preferably from 0.2 to 1 μm, more preferably from 0.3 to 0.8 μm. If the average particle size exceeds 1 μm, the absorbability through the gut tends to deteriorate.

The benzoyl urea compound having the specified particle size of the present invention can be prepared, for instance, by pulverizing the benzoyl urea compound (I) or (II) in an aqueous solution containing a dispersant such as a nonionic surfactant. There is no particular restriction as to the nonionic surfactant to be used for this purpose. Any nonionic surfactant may be employed so long as it is useful as an additive for pharmaceuticals. Its HLB value (Hydrophile-Lipophile Balance) is preferably at least 3. Specific examples of such nonionic surfactants include polyoxyethylene hardened caster oil 20, polyoxyethylene hardened caster oil 40, polyoxyethylene hardened caster oil 60, polyoxyethylene hardened caster oil 100, polysorbate 60, polysorbate 65, polysorbate 80, polyoxyethylene polyoxypropylene glycol, a sucrose fatty acid ester, a glycerol fatty acid ester, a sorbitan fatty acid ester, a propylene glycol fatty acid ester, a polyglycerol fatty acid ester, a polyoxyethylene sorbitan fatty acid ester, a polyoxyethylene sorbitol fatty acid ester, a polyoxyethylene glycerol fatty acid ester, a polyethylene glycol fatty acid ester and a polyoxyethylene castor oil.

The pulverization is preferably conducted by wet pulverization. The wet pulverization is a method wherein the material to be pulverized is rotated or shaken together with beads (particularly glass beads) in a solution containing the dispersant. A machine such as Dyno-mill (KDL-model, manufactured by Willy A. Bachofen Company) may be employed for this purpose. The concentration of the benzoyl urea compound in the aqueous solution during the pulverization, is from 1 to 70 w/v%, preferably from 20 to 50 w/v%. Particularly when the pulverization is conducted in a wet pulverization system by using Dyno-mill, the concentration of the benzoyl urea compound in the aqueous solution is preferably within the above range. The concentration of the nonionic surfactant as a dispersant is usually from 1 to 30 w/v%, preferably from 2 to 20 w/v%. The glass beads employed usually have a size of from 0.1 to 1.5 mm in diameter, preferably from 0.25 to 0.5 mm in diameter. The pulverization time is usually from 5 minutes to 1 hour, preferably from 30 minutes to 1 hour. After the completion of the wet pulverization, glass beads will be removed by sieving, and if necessary additives such as a sweetening agent or a perfume may be added thereto. If necessary, the composition is then subjected to autoclave sterilization or to filtration for the removal of bacteria, to obtain the benzoyl urea compound dispersed in water (which will be referred to as a liquid composition).

Further, the benzoyl urea compound of the present invention may be formed into a dry formulation, if necessary. The dry formulation may be prepared by freeze-drying the above liquid composition by a usual method, preferably after an addition of a suitable amount of a disintegrator. As such a disintegrator, saccharides, saccharide alcohols, silicic anhydride or a nonionic surfactant (the same as mentioned above) may be employed. Particularly preferred is a nonionic surfactant. The saccharides as a disintegrator include a monosaccharide such as glucose or fructose, a disaccharide such as sucrose, maltose or lactose and a polysaccharide such as starch, dextrin or cellulose. The saccharide alcohols include, for example, xylitol, mannitol and sorbitol.

The silicic anhydride as the disintegrator is preferably a light anhydrous silicic acid.

The nonionic surfactant as the disintegrator is preferably those exemplified above as a dispersant, more preferably a sucrose fatty acid ester or a polyoxyethylene polyoxypropylene glycol. The nonionic surfactant can be used both as the dispersant and as the disintegrator, preferably used differently as each of them. For instance, in the case of using polyglycerol fatty acid ester (e.g. decaglycerol monolaurate) or polyoxyethylene hardened caster oil (e.g. polyoxyethylene hardened caster oil 60) as the dispersant, a sucrose fatty acid ester is preferably used as the disintegrator.

The amount of disintegrator is added preferably in an amount of from 1 to 90 w/v%, more preferably from 20 to 70 w/v%.

Thus, it is possible to obtain a formulation having excellent granularity as a dry formulation and having excellent dispersibility in water.

In the preparation of the present invention, the ratio of the benzoyl urea compound to be dispersant and the disintegrator is, for instance, the benzoyl urea compound:the dispersant:the disintegrator = 1-70:1-30:1-90 by weight, preferably 20-50:2-20:10-70 by weight.

The benzoyl urea compound of the present invention can be formulated into other pharmaceutical formulations by conventional methods. As such pharmaceutical formulations, oral formulations such as powders, fine particles, granules, capsules, tablets and liquid drugs may be mentioned.

Such formulations may be prepared by removing water from the above-mentioned liquid composition by heat drying, freeze drying, centrifugal separation, membrane filtration, etc., and then following a conventional method for formulation by using or without using conventional pharmaceutical additives.

The benzoyl urea compound having the specified particle size of the present invention may usually orally be administered to mammals (e.g. human beings, horses, cattles, dogs, mice, rats, etc.). The dose varies depending upon the diseases condition, the sex, the body weight, the formulation, etc. However, for instance, when the benzoyl urea compound of the present invention is orally administered against human malignant lymphoma or lung cancer, the benzoyl urea compound is administered in a daily dose of from 5 to 100 mg/kg to an adult in one to three times per week.

With the benzoyl urea compound having the specified particle size of the invention, the absorption through the gut is remarkably improved, and the stability of the particles in a liquid state is excellent.

By using the benzoyl urea compound having the specified particle size according to the present invention, it is possible to reduce the dose of the benzoyl urea compound and thus to reduce the side effects or the pain to the the patient when it is administered to the patient.

TEST EXAMPLE 1 (Formulation Conditions)

(1) Type of the benzoyl urea compound

Compound No. 3, No. 5 or No. 6 (4 w/v%) as the benzoyl urea compound and polyoxyethylene hardened caster oil 60 (HCO-60, manufactured by Nikko Chemical K.K., 10 w/v%) as a dispersant were suspended in water, and after an addition of glass beads (from 1 to 1.4 mm in diameter) in an amount of the same volume, subjected to rotary pulverization by Dyno-mill for 20 minutes. The average particle size of the benzoyl urea compound thus obtained was measured and shown in Table 1.

TABLE 1

| Sample*[1] | Particle size (μm) |
|---|---|
| Compound No. 3 | 0.43 |
| Compound No. 5 | 1.13 |

TABLE 1-continued

| Sample*[1] | Particle size (μm) |
|---|---|
| Compound No. 6 | 0.72 |

*[1]Benzoyl urea compound

The average particle size was measured in such a manner that the benzoyl urea compound was diluted to a concentration of 20 μg/ml and the average particle size was measured by a light scattering method (Autosizer, Model 700, manufactured by Maruburn Company) (the same applies hereinafter).

(2) Type of the dispersant

Compound No. 3 (4 w/v%) and the following dispersant (10 w/v%) were suspended in water, and after an addition of glass beads (from 1 to 1.4 mm in diameter) in an amount of the same volume, subjected to rotary pulverization by Dyno-mill for 45 minutes. As the dispersant, polyoxyethylene hardened caster oil 60 (HCO-60, manufactured by Nikko Chemical K.K.), polyoxyethylene (160) polyoxypropylene (30) glycol (F68, manufactured by Asahi Denka Kogyo K.K.), a decaglycerol fatty acid ester (Decagly.ester, Nikko Chemical K.K.) or polysolbate 80 (Tween 80, manufactured by Nakarai Kagaku K.K.) was employed.

TABLE 2

| Dispersant | Particle size (μm) |
|---|---|
| HCO-60 | 0.9 |
| F68 | 0.9 |
| Decagly.ester | 0.6 |
| Tween 80 | 0.6 |

(3) Concentration of the benzoyl urea compound

Compound No. 3 (from 10 to 40 w/v%), HCO-60 (5 w/v%) as a dispersant and glass beads (from 1 to 1.5 mm in diameter) were subjected to rotary pulverization by Dyno-mill for pulverization time of 30 minutes. Then, the average particle size of the benzoyl urea compound was measured.

TABLE 3

| Sample (w/v %) | Particle size (μm) |
|---|---|
| 10 | 0.56 |
| 20 | 0.50 |
| 40 | 0.46 |

(4) Concentration of the dispersant

Compound No. 3 (20 w/v%), HCO-60 (from 2.5 to 10 w/v%) as the dispersant and glass beads (from 1 to 1.5 mm in diameter) were subjected to rotary pulverization by Dyno-mill for a pulverization time of 30 minutes. Then, the average particle size of the benzoyl urea compound was measured.

TABLE 4

| Dispersant (w/v %) | Particle size (μm) |
|---|---|
| 2.5 | 0.54 |
| 5 | 0.50 |
| 10 | 0.45 |

(5) Size of beads

Compound No. 3 (40 w/v%), HCO-60 (5 w/v%) as the dispersant and glass beads (three types having a diameter of from 0.25 to 0.5, from 0.5 to 0.75 and from 1 to 1.5 mm, respectively) were subjected to rotary pulverization by Dyno-mill for a pulverization time of 30 minutes. Then, the average particle size of the benzoyl urea compound was measured.

TABLE 5

| Diameter of beads (mm in diameter) | Particle size (μm) |
| --- | --- |
| 0.25–0.5 | 0.30 |
| 0.5–0.75 | 0.33 |
| 1–1.5 | 0.46 |

(6) Pulverization time

Compound No. 3 (40 w/v%), HCO-60 (5 w/v%) as the dispersant and glass beads (from 0.25 to 0.5 mm in diameter), were subjected to rotary pulverization by Dyno-mill for a pulverization time of from 10 to 60 minutes. Then, the average particle size of the benzoyl urea compound was measured.

TABLE 6

| Pulverization time (minutes) | Particle size (μm) |
| --- | --- |
| 10 | 0.38 |
| 20 | 0.33 |
| 30 | 0.29 |
| 40 | 0.27 |
| 50 | 0.26 |
| 60 | 0.26 |

TEST EXAMPLE 2

The stability of particles in the liquid composition of the benzoyl urea compound was investigated.

Namely, a wet pulverization formulation comprising compound No. 3 (40 w/v%) and HCO-60 (10 w/v%) was stored at room temperature, whereby the stability of the particles was investigated. The results are shown in Table 7.

TABLE 7

| Storage duration (months) | Particle size (μm) |
| --- | --- |
| 0 | 0.7 |
| 1 | 0.8 |
| 3 | 1.3 |

TEST EXAMPLE 3

Each of four wet pulverized formulations having different particle sizes [composition: Compound No. 3 (40 w/v%) and HCO-60 (10 w/v%)] was forcibly orally administered by an oral sonde to a group of 5 Wister male rats (body weight: 200 g) starved for 18 hours (dose: 50 mg/5 ml/kg). Then, blood (0.3 ml) was periodically sampled with heparin from the jugular vein.

The blood thus obtained was subjected to separation of the plasma and removal of proteins by using acetonitrile, and then Compound No. 3 was quantitatively analyzed by a high speed liquid chromatography using a reversed phase column (Nova Pak $C_{18}$, 5μ, 3.9 mm in diameter × 150 mm, Nihon Waters), and the curve of the concentration in blood was prepared.

From the curve of the concentration in blood, the area below the curve was obtained by using a trapezoid formula and presented as AUC (Area Under the Curve).

TABLE 8

| Particle size (μm) | AUC (0–24 hr) (μg/ml. hr.) |
| --- | --- |
| 0.31 | 11.6 ± 2.3 |
| 0.66 | 10.0 ± 1.6 |
| 1.5 | 8.1 ± 1.2 |
| 2.5 | 6.9 ± 1.4 |

EXAMPLE 1

Compound No. 3 (20 g) was suspended in 50 ml of a 5 w/v% HCO-60 aqueous solution, and the suspension was wet pulverized (3000 rpm for 45 minutes) by Dyno-mill by using 50 g of glass beads (from 0.25 to 0.5 mm in diameter). After the completion of the pulverization, glass beads were removed by sieving, to obtain a wet pulverized formulation of Compound No. 3.

The wet pulverized formulation thus obtained was sterilized in an autoclave to obtain a liquid formulation of a final form. The average particle size of Compound No. 3 in this liquid formulation was 0.68 μm. Instead of the sterilization in an autoclave, it is possible to employ filtration to remove bacteria. If necessary, a sweetening agent, a perfume, etc. may be added.

EXAMPLE 2

To 50 ml of the liquid formulation obtained in Example 1, 20 g of a sucrose fatty acid ester (P1670, manufactured by Mitsubishi Chemical Industries, Ltd.) was added. The mixture was freezed with dry ice-methanol and then subjected to vacuum drying for 24 hours to remove water. The solid thus obtained was filled in capsules to obtain capsule drugs.

EXAMPLE 3

Compound No. 3 (15 g) was suspended in 50 ml of a 5 w/v% decaglycerol monolaurate (Decagline 1 L, manufactured by Nikko Chemical K.K.) aqueous solution, and the suspension was wet pulverized (3000 rpm for 45 minutes) by Dyno-mill by using 50 g of glass beads (from 0.25 to 0.5 mm in diameter). After the completion of the pulverization, glass beads were removed by sieving, to obtain a wet pulverized formulation of Compound No. 3.

The wet pulverized formulation thus obtained was sterilized in an autoclave to obtain a liquid formulation of a final form. The average particle size of Compound No. 3 in this liquid formulation was 0.75 μm. Instead of the sterilization in an autoclave, it is possible to employ filtration to remove bacteria. If necessary, a sweetening agent, a perfume, etc. may be added.

EXAMPLE 4

To 50 ml of the liquid formulation obtained in Example 3, 30 g of a sucrose fatty acid ester (P1670, manufactured by Mitsubishi Chemical Industries, Ltd.) was added. The mixture was freezed with dry ice-methanol and then subjected to vacuum drying for 24 hours to remove water. The solid thus obtained was filled in capsules to obtain capsule drugs.

We claim:

1. A benzoyl urea compound have the formula:

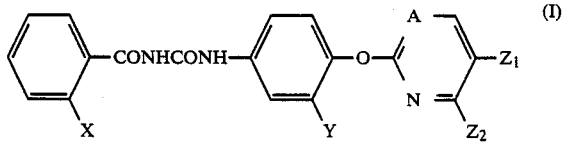

(I)

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a nitrogen atom, characterized in that its average particle size is not larger than 1 μm.

2. The benzoyl urea compound according to claim 1, which is N-(2-nitrobenzoyl)-N'-[3-chloro-4-(5-bromo-2-pyrimidinyloxy)phenyl]urea.

3. The benzoyl urea compound according to claim 1, of which an average particle size is within a range of from 0.2 to 1 μm.

4. An antitumor composition comprising an effective amount of the benzoyl urea compound according to claim 1, which is suspended in an aqueous solution containing a dispersant.

5. The benzoyl urea compound according to claim 1, which is prepared by pulverization in an aqueous solution containing a nonionic surfactant as a dispersant.

6. The benzoyl urea compound according to claim 5, wherein the nonionic surfactant as a dispersant has at least 3 HLB value.

7. The benzoyl urea compound according to claim 5, wherein the nonionic surfactant as a dispersant is at least one selected from the group consisting of polyoxyethylene hardened caster oil 20, polyoxyethylene hardened caster oil 40, polyoxyethylene hardened caster oil 60, polyoxyethylene hardened caster oil 100, polysorbate 60, polysorbate 65, polysorbate 80, polyoxyethylene polyoxypropylene glycol, a sucrose fatty acid ester, a glycerol fatty acid ester, a sorbitan fatty acid ester, a propylene glycol fatty acid ester, a polyglycerol fatty acid ester, a polyoxyethylene sorbitan fatty acid ester, a polyoxyethylene sorbitol fatty acid ester, a polyoxyethylene glycerol fatty acid ester, a polyethylene glycol fatty acid ester and a polyoxyethylene caster oil.

8. An antitumor composition comprising an effective amount of the benzoyl urea compound according to claim 1, which is in the form of a freeze-dried formulation.

9. An antitumor composition comprising an effective amount of the benzoyl urea compound according to claim 1, which is in the form of a freeze-dried formulation after an addition of a suitable amount of a disintegrator.

* * * * *